(12) United States Patent
Yueh et al.

(10) Patent No.: US 9,663,751 B2
(45) Date of Patent: May 30, 2017

(54) PLATFORM SYSTEM FOR IN VITRO CELL CO-CULTIVATION WITH AUTOMATIC TRAPPING FUNCTION

(71) Applicant: NATIONAL TSING HUA UNIVERSITY, Hsinchu (TW)

(72) Inventors: Ting-Ju Yueh, Hsinchu (TW); Chi-Fan Chen, Douliu (TW); Kuo-Wei Chang, Zhudong Township, Hsinchu County (TW); Pei-Yu Chang, Tainan (TW); Cheng-Hsien Liu, Hsinchu (TW); Hong-Yuan Huang, Taipei (TW); Chin-Jung Li, Hsinchu (TW); Chang-Hung Tien, New Taipei (TW); Da-Jeng Yao, Hsinchu (TW); Shih-Kang Fan, Taipei (TW); Wen-Syang Hsu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 190 days.

(21) Appl. No.: 14/588,533

(22) Filed: Jan. 2, 2015

(65) Prior Publication Data
US 2015/0291926 A1 Oct. 15, 2015

(30) Foreign Application Priority Data

Apr. 10, 2014 (TW) .............................. 103113163 A (51) Int. Cl.
*C12M 1/00* (2006.01)
*C12M 3/00* (2006.01)
(Continued)

(52) U.S. Cl.
CPC ............ *C12M 23/34* (2013.01); *C12M 21/06* (2013.01); *C12M 21/08* (2013.01); *C12M 23/04* (2013.01);
(Continued)

(58) Field of Classification Search
CPC . A23D 9/00; A23D 9/007; A23D 9/02; A23K 10/38; C07C 53/00; C07C 57/12;
(Continued)

(56) References Cited

U.S. PATENT DOCUMENTS

7,754,474 B2 * 7/2010 Aysta .................. B01L 3/50851
374/24
8,076,129 B2 * 12/2011 Hanafusa .............. B01L 3/5025
435/289.1
(Continued)

*Primary Examiner* — Michael Hobbs
(74) *Attorney, Agent, or Firm* — Muncy, Geissler, Olds & Lowe, P.C.

(57) ABSTRACT

The present disclosure illustrates a platform system for in vitro cell co-cultivation with automatic trapping function. The platform system aims to develop a bio-chip applied in cell culture systems, and has several features. The first feature is that this co-cultivation platform can construct a micro environment suitable for culture of various cells. The second feature is dynamic perfusion. The microfluidic system is used to dynamically replace the culture medium, in order to maintain an appropriate environment for the growth of cells. The third feature is the automatic trapping. The cells to be cultured can be trapped in a suitable location according to the flow resistance, so that the damaged on the cell caused by manual operation can be minimized.

9 Claims, 6 Drawing Sheets (51) Int. Cl.
*C12M 3/06* (2006.01)
*C12M 1/12* (2006.01)
*C12M 1/32* (2006.01)
*C12M 1/42* (2006.01)

(52) U.S. Cl.
CPC ............ *C12M 23/12* (2013.01); *C12M 23/16* (2013.01); *C12M 23/58* (2013.01); *C12M 29/10* (2013.01); *C12M 35/08* (2013.01)

(58) Field of Classification Search
CPC ........ C10L 3/026; C11B 13/00; C11B 5/0007; C11B 5/0092; C12F 3/10; Y02E 50/13; Y02W 30/74
See application file for complete search history.

(56) References Cited

U.S. PATENT DOCUMENTS

| | | | |
|---|---|---|---|
| 8,187,863 B2* | 5/2012 | Sim | B01L 3/502715 422/72 |
| 2006/0275852 A1* | 12/2006 | Montagu | B01L 3/502715 435/7.93 |
| 2011/0015416 A1* | 1/2011 | Ueyama | A23D 9/00 554/63 |
| 2011/0262906 A1* | 10/2011 | Dimov | B01L 3/50273 435/6.1 |

* cited by examiner

PLATFORM SYSTEM FOR IN VITRO CELL CO-CULTIVATION WITH AUTOMATIC TRAPPING FUNCTION

CROSS-REFERENCE TO RELATED APPLICATION

This application claims the benefit of Taiwan Patent Application No. 103113163, filed on Apr. 10, 2014, in the Taiwan Intellectual Property Office, the disclosure of which is incorporated herein in its entirety by reference.

BACKGROUND OF THE INVENTION

1. Field of the Invention

The present disclosure illustrates a cell co-cultivation platform system, in particular, to a platform system for in vitro cell co-cultivation with automatic trapping function which can be applied in a bio-chip for cell culture system, so that the processes for cell co-cultivation can be reduced and the cells can be trapped automatically by using microfluidic technology.

2. Description of the Related Art

Cell culture is an important section in bio-technology. However, the traditional culture technology still uses petri dish for drop culture. It is easy to control the cultivation parameter in the single cell culture, but the mutual effect between various cells in real is ignored. Moreover, the cultivation environment in the petri dish cannot simulate a cultivation environment efficiently, it causes the quality of the cultivated cell is not good enough.

Some persons disclose that the bio-chip can be used to improvement cultivation quality. In addition, when the cell to be cultivated is applied by a physical stimulation, such as electric field, flow field, magnetic field, temperature field, or combination thereof, the quality of cultivated cell can be improved efficiently. However, the good or bad for various stimulation parameters is not determined.

Moreover, the cell trapping in the bio-chip is not good enough. In prior art, the cell is arranged by manually, so the cell is easy to be damaged due to the clamp force, and the quality of cultivation is impaired.

SUMMARY OF THE INVENTION

To solve the above-mentioned problems, one of objectives of the present disclosure is to provide a platform system for in vitro cell co-cultivation with automatic trapping function which uses microfluidic technology to reduce co-cultivation processes and automatically trap cells.

To solve the above-mentioned problems, another objective of the present disclosure is to provide a platform system for in vitro cell co-cultivation with automatic trapping function which integrates functions of cell co-cultivation, dynamic perfusion, cells trapping and cells positioning, and further simplifies IC process, structure and operation step, in order to construct a micro environment suitable for cell growth to achieve purpose of cell culture.

To solve the above-mentioned problems, another objective of the present disclosure is to provide a platform system for in vitro cell co-cultivation with automatic trapping function which can replace the culture medium timely by dynamic perfusion, to prevent the excrement of the cell or death cell from heaping in the cell co-cultivation platforms to impair the quality of cultivation.

To solve the above-mentioned problems, another objective of the present disclosure is to provide a platform system for in vitro cell co-cultivation with automatic trapping function which can improve the detection efficiency and decrease impairment caused by manual operation.

An exemplary embodiment of the present disclosure provides a platform system for in vitro cell co-cultivation with automatic trapping function which comprises a dynamic culture flow channel module, a plurality of cell co-cultivation platforms, a trapping flow channel module and a control module.

The dynamic culture flow channel module comprises a culture medium infusion end, a culture medium recovery end and a plurality of perfusion flow channels. Ends of the plurality of perfusion flow channels are radially arranged around the culture medium infusion end, and other ends of the plurality of perfusion flow channels are converged to the culture medium recovery end. The plurality of cell co-cultivation platforms are for co-cultivation of a plurality of base cells and a plurality of cell to be cultivated. The plurality of cell co-cultivation platforms are arranged around the culture medium infusion end. The plurality of perfusion flow channels are respectively passed through by the plurality of perfusion flow channels to correspondingly form a plurality of cell trapping areas.

The trapping flow channel module comprises a cell infusion end, a cell inhalation end and a cell flow channel. The cell flow channel surrounds annularly and passes through the plurality of cell co-cultivation platforms, and surrounds outer side of cell co-cultivation platforms, and is connected with the perfusion flow channels.

When a cell trapping process is performed, the control module closes the culture medium infusion end and the culture medium recovery end, and opens the cell infusion end and the cell inhalation end. The control module then infuses the cells to be cultivated into the cell infusion end. The cells to be cultivated flow through the cell co-cultivation platforms via the cell flow channel, and respectively stop at corresponding the cell trapping areas according to difference between dynamic flow resistances. After the cells to be cultivated are respectively trapped at the cell trapping areas, the control module closes the cell infusion end and the cell inhalation end, and opens the culture medium infusion end and the culture medium recovery end, and then infuses the culture medium via the culture medium infusion end to perform a dynamic perfusion culture process for co-cultivation of the cells.

Preferably, the cells to be cultivated comprise embryonic cell, organ and tissue cell or stem cell.

Preferably, the base cells are a cell population for co-cultivation corresponding to the cells to be cultivated.

Preferably, structural size of each of the cell trapping area is smaller than size of each of the corresponding cells to be cultivated.

Preferably, when an initial culture process is performed on the cell co-cultivation platforms, the control module closes the cell infusion end and the cell inhalation end first, and then infuses the culture medium containing the base cells via the culture medium infusion end. The culture medium flows into the cell co-cultivation platforms, and the base cell respectively attach to the cell co-cultivation platforms to perform the initial culture process.

Preferably, after the cell to be cultivated are trapped at the cell trapping areas, the cells not trapping at the cell trapping areas are recovered at the cell inhalation end.

Preferably, the control module infuses the culture medium via the perfusion flow channels, to flush the cells to be cultivated, to return the cells to be cultivated to the culture medium infusion end for further extraction.

Preferably, the infused fluid flow of the cells to be cultivated is from 0.05 to 10 µl/min.

Preferably, the infused fluid flow of the culture medium in dynamic perfusion culture process is from 0.01 to 5 µl/min.

The present disclosure provides a platform system for in vitro cell co-cultivation with automatic trapping function, and the platform system has the following advantages.

The first advantage is that the platform system of the present disclosure can construct a micro environment suitable for cell growth by using different microfluidic structure, to achieve the purpose of cell culture.

The second advantage is that the platform system of the present disclosure can construct a platform for culture of various cells, and be used to simulate interactive effects between various cells during culture process, to improve the drawback in traditional technology for only one cell culture.

The third advantage is that the platform system of the present disclosure can an stimulate the cells to be cultivated during the replacement process for the culture medium, except dynamically discarding the culture medium, so as to improve the quality and efficiency of culture of for the cells to be cultivated.

The fourth advantage is that the platform system of the present disclosure designs the micro flow channel structure upon the calculation of dynamic flow resistance in the microfluidic system in order to automatically trap the cells in the preset areas under appropriate driving flow speed and prevent the cells from being damaged.

The fifth advantage is that the cell co-cultivation platforms are annularly arranged, so the turbulent flow can be reduced efficiently and the external force impairment caused by the shearing stress of the flow applied on the cells can be reduced. Therefore, the quality of cell culture can be improved.

BRIEF DESCRIPTION OF THE DRAWINGS

The detailed structure, operating principle and effects of the present disclosure will now be described in more details hereinafter with reference to the accompanying drawings that show various embodiments of the present disclosure as follows.

DETAILED DESCRIPTION OF THE PREFERRED EMBODIMENTS

Reference will now be made in detail to the exemplary embodiments of the present disclosure, examples of which are illustrated in the accompanying drawings. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this disclosure will be thorough and complete, and will fully convey the inventive concept to those skilled in the art. The relative proportions and ratios of elements in the drawings may be exaggerated or diminished in size for the sake of clarity and convenience in the drawings, and such arbitrary proportions are only illustrative and not limiting in any way. The same reference numbers are used in the drawings and the description to refer to the same or like parts.

It will be understood that, although the terms 'first', 'second', 'third', etc., may be used herein to describe various elements, these elements should not be limited by these terms. The terms are used only for the purpose of distinguishing one component from another component. Thus, a first element discussed below could be termed a second element without departing from the teachings of embodiments. As used herein, the term "or" includes any and all combinations of one or more of the associated listed items.

Figure 1:
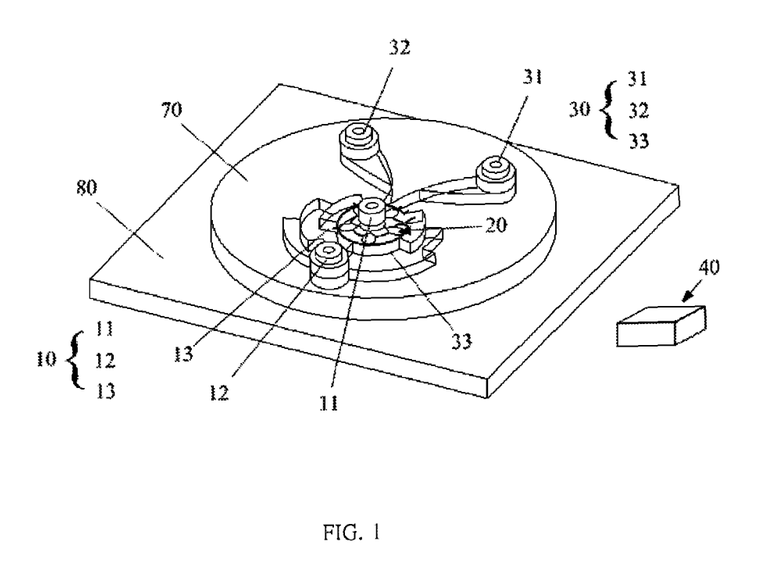
FIG. 1 a structural schematic view of an IC flow channel system of a platform system for in vitro cell co-cultivation with an automatic trapping function of the present disclosure.
Figure 2:
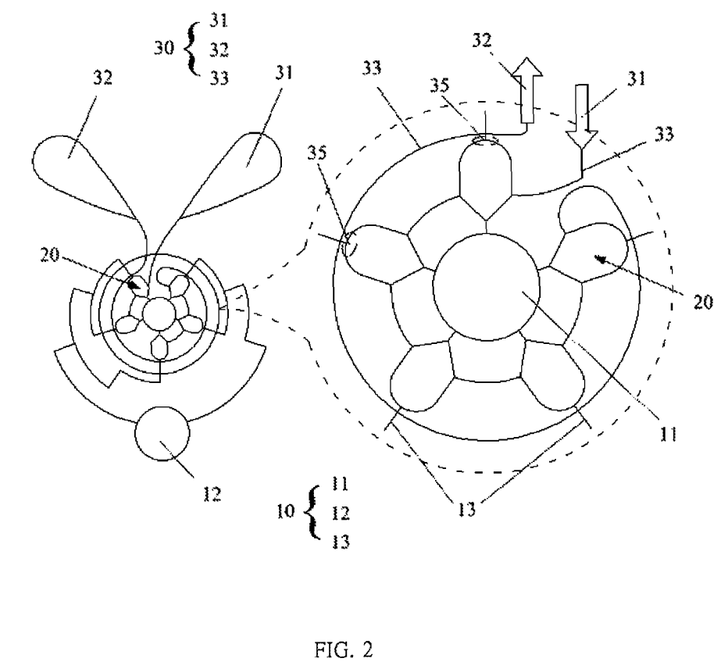
FIG. 2 a schematic view of the IC flow channel system of a platform system for in vitro cell co-cultivation with the automatic trapping function of the present disclosure.

Please refer to FIG. 1 and FIG. 2. A platform system for in vitro cell co-cultivation with automatic trapping function comprises a dynamic culture flow channel module 10, a cell co-cultivation platform 20, a trapping flow channel module 30 and a control module 40. The dynamic culture flow channel module 10 comprises a culture medium infusion end 11, a culture medium recovery end 12 and a plurality of perfusion flow channels 13. Ends of the perfusion flow channels 13 are radially arranged around the culture medium infusion end 11 and other ends of the perfusion flow channels 13 are converged to the culture medium recovery end 12.

The cell co-cultivation platforms 20 provide areas for co-cultivation of a plurality of base cells 51 and a plurality of cells 50 to be cultivated. The cell co-cultivation platforms 20 are annularly arranged around the culture medium infusion end 11. The cell co-cultivation platforms 20 are respectively passed through by the plurality of perfusion flow channels 13 to correspondingly form a plurality of cell trapping areas 35 in the cell co-cultivation platforms 20.

The trapping flow channel module 30 comprises a cell infusion end 31, a cell inhalation end 32 and a cell flow channel 33. The cell flow channel 33 surrounds annularly and passes through the cell co-cultivation platforms 20, and surrounds outer side of the cell co-cultivation platforms 20, and is connected with the perfusion flow channels 13.

The control module 40 controls each of operation steps for the platform system for in vitro cell co-cultivation with automatic trapping function. Therefore, the operator can manually control the control module 40 at the cultivation stage, or the control module 40 can be programmable operated automatically by an automatic apparatus, so as to decrease the impairment caused by the manual operation and increase the efficiency of cell cultivation.

The platform system for in vitro cell co-cultivation with automatic trapping function of the present disclosure can be implemented by IC. The master batch mold of the flow channel system can be built by photoresist development, and the master batch mold is used to make casting of the external mold 70 of the flow channel system by a soft mold imprint process, and the external mold 70 is combined on the substrate 80 for movable detection. The substrate 80 can be acrylic substrate or glass substrate.

Preferably, the material of external mold 70 of the flow channel system is biological compatibility polymer material which comprises PMMA, PE, silicone rubber or polydimethylsiloxane, polyester, PTFE, PDMS, PU, collagen, gelatin, hyaluronic acid, chitin, chitosan, alginate, cellulose and derivative thereof.

Figure 3:
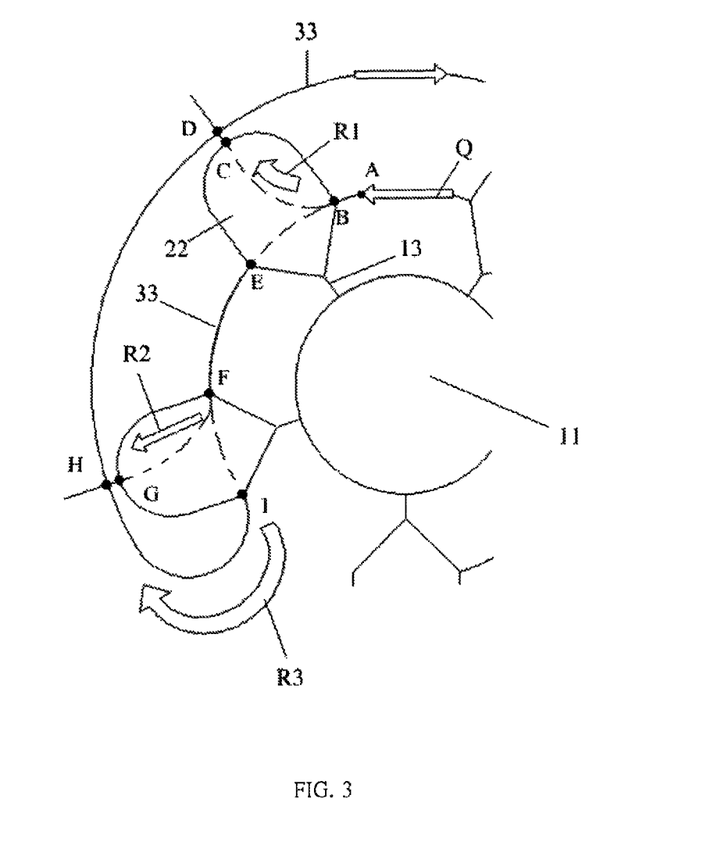
FIG. 3 a schematic view of concept of dynamic flow resistance of the platform system for in vitro cell co-cultivation with the automatic trapping function of the present disclosure.

Please refer to FIG. 3. The present disclosure utilizes dynamic flow resistance to automatically trap the cells in the cell trapping area 35. The microfluidic structure is designed upon the calculation of dynamic flow resistance in the microfluidic system, in order to automatically trap the cells in the preset areas under appropriate driving flow speed and prevent the cells from being damaged. The detail description is in the following paragraph.

When the cell infusion end 31 is infused fluid flow Q to the cell flow channel 33, a first path R1 passes node A, node B, node C and node D of the flow channel system in sequence. The first path R1 has smaller flow resistance and larger flow, so the cell can be trapped first in the cell trapping area 35 formed by the cell co-cultivation platform 20 and the perfusion flow channel 13. As shown in the FIG. 3, the node C of the flow channel system is the cell trapping area 35.

When the cell is automatically trapped in node C of the flow channel system, the node C of the flow channel system is blocked which causes the flow resistance increases, so the fluid flow Q flows through a second path R2 formed by the node A, node B, node E, node F, node G, node H and node D of the flow channel system, and the next cell is trapped at the node G of the flow channel system.

When all cell trapping areas 35 are blocked by the cells, the fluid flow Q flow through a third path R3 formed by node A, node B, node E, node F, node I, node H and node D, so the cells not being trapped are converged to the cell inhalation end 32 through the cell flow channel 33 for recovery.

Figure 4:
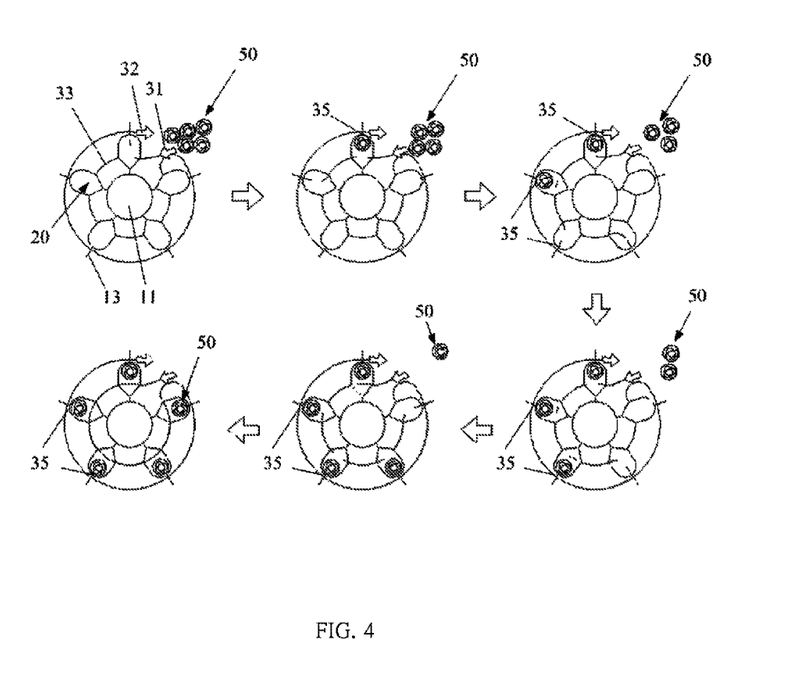
FIG. 4 a flow schematic view of cell trapping of the platform system for in vitro cell co-cultivation with the automatic trapping function of the present disclosure.

Please refer to FIG. 4 which is a schematic view of cell trapping in accordance with the present disclosure. When a trapping process for the cells 50 to be cultivated is performed, the control module 40 closes the culture medium infusion end 11 and the culture medium recovery end 12 to make the dynamic culture flow channel module 10 being closed status. The control module 40 then opens the cell infusion end 31 and the cell inhalation end 32 to make the cell flow channel 33 unobstructed. The control module 40 then infuses the cells 50 to be cultivated into the cell infusion end 31. The cells 50 to be cultivated can flow through the cell co-cultivation platforms 20 via the cell flow channel 33, and respectively stop at the corresponding cell trapping areas 35 according to difference between dynamic flow resistances.

The structural size of each of the cell trapping areas 35 is smaller than size of each of the corresponding cells 50 to be cultivated. In addition, the structure of the cell trapping area 35 can be single-layer structure or multiple-layer structure to adjust the size of opening where the perfusion flow channel 13 passing through the cell co-cultivation platform 20.

Figure 5:
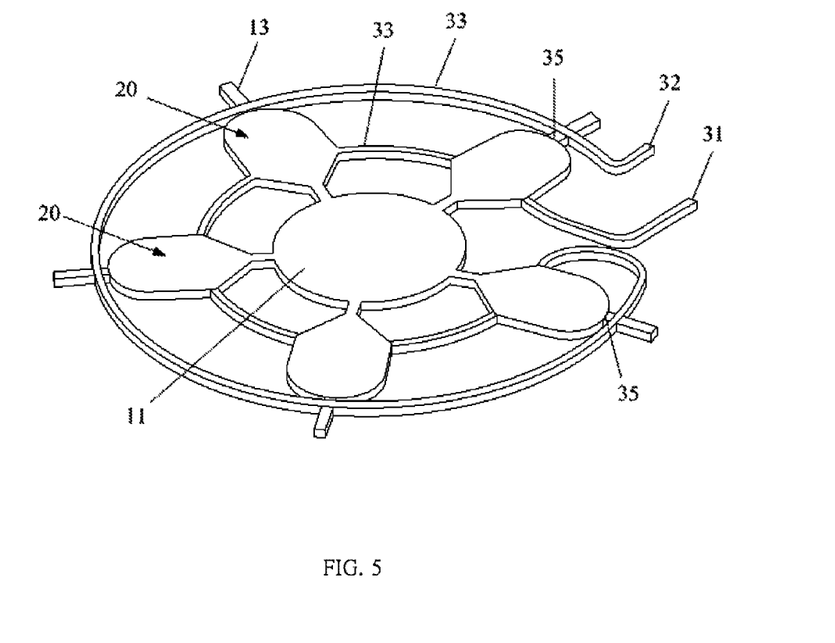
FIG. 5 a schematic view of a co-cultivation platform flow channel of the platform system for in vitro cell co-cultivation with automatic trapping function of the present disclosure.

Please refer to FIG. 5, the cell co-cultivation platforms 20 provide areas for co-cultivation of the base cells 51 and the cells 50 to be cultivated. The cell co-cultivation platforms 20 are annularly arranged around the culture medium infusion end 11. The cell co-cultivation platforms 20 are respectively passed through by the plurality of perfusion flow channels 13 to correspondingly form the cell trapping areas 35 in the cell co-cultivation platforms 20. The number of the cell co-cultivation platforms 20 of this exemplary embodiment is five as an example, but the present disclosure is not limited thereto. The cell co-cultivation platforms 20 are annularly arranged, so the turbulent flow can be reduced efficiently and the external force impairment caused by the shearing stress of the flow applied on the cells 50 can be reduced. Therefore, the quality of cell culture can be improved. The cells 50 to be cultivated comprise an embryonic cell, an organ and tissue cell or a stem cell. The base cell 51 is a cell population for co-cultivation corresponding to the cells 50.

Figure 6:
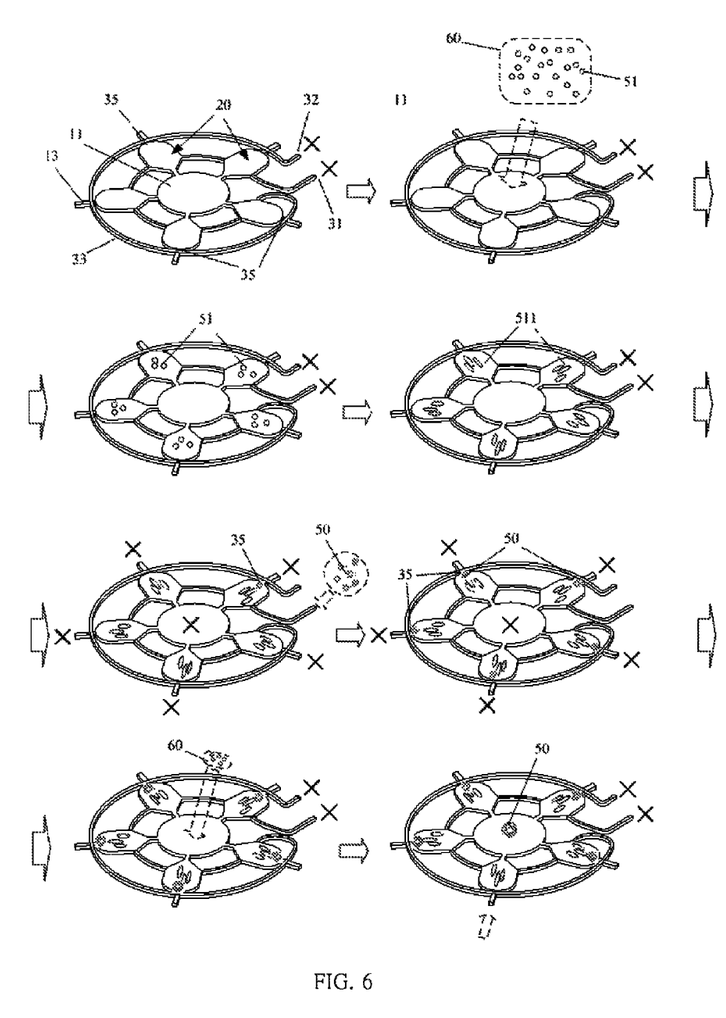
FIG. 6 a flow schematic view of in vitro cell cultivation of the platform system for in vitro cell co-cultivation with the automatic trapping function of the present disclosure.

Please refer to FIG. 6 which is in vitro a schematic view of in vitro cell cultivation in accordance with the present disclosure. The process of in vitro cell cultivation comprises the following steps. when an initial culture process is performed on a plurality of cell co-cultivation platforms 20, the control module 40 closes the cell infusion end 31 and the cell inhalation end 32 first, and then infuses a culture medium 60 containing base cells 51 via the culture medium infusion end 11. The culture medium 60 flows and disperses the cell co-cultivation platforms 20 via the perfusion flow channels 13, so the base cells 51 attaches to the cell co-cultivation platforms 20 for performing the initial culture process.

After being cultured by dynamic perfusion for a period of time, the base cells 51 attaching in the cell co-cultivation platforms 20 are cultivated to the growth base cells 511. The growth base cells 511 fill inside the cell co-cultivation platform 20 to construct a micro environment suitable for growth of the cells 50. The cell co-cultivation platform 20 is used to simulate interactive effects between various cells during culture process, to improve the drawback in traditional technology for only one cell culture.

After the construction of the micro environment is completed, the trapping process for the cells 50 to be cultivated is performed. The control module 40 closes the culture medium infusion end 11 and the culture medium recovery end 12 first, and opens the cell infusion end 31 and the cell inhalation end 32, and then infuse the cells 50 to be cultivated from the cell infusion end 31. The cells 50 to be cultivated flow through the cell co-cultivation platforms 20 via the cell flow channel 33, and respectively stay in corresponding cell trapping areas 35 according to difference of the dynamic flow resistance. In implementation, the infused fluid flow of the cells 50 to be cultivated may be from 0.05 to 10 μl/min.

After the cells 50 to be cultivated are automatically trapped at the cell trapping areas 35 respectively, the cells not trapped at the cell trapping areas 35 flow to the cell inhalation end 32 for recovery.

After the cells 50 to be cultivated are respectively trapped at the cell trapping areas 50, the control module 40 closes the cell infusion end 31 and the cell inhalation end 32, and opens the culture medium infusion end 11 and the culture medium recovery end 12. The control module 40 then infuses the culture medium 60 via the culture medium infusion end 11 to perform a dynamic perfusion culture process for co-cultivation of the cells. The kind of the culture medium 60 can be adjusted and replaced according to corresponding culture step. Except dynamically discarding the culture medium 60, the dynamic perfusion culture process further can stimulate the cells 50 to be cultivated 50 during the replacement process for the culture medium 60, to improve the quality and efficiency of culture for the cell 50 to be cultivated. In implementation, the infused fluid flow of the culture medium 60 in dynamic perfusion culture process may be from 0.01 to 5 μl/min.

When growth of the cells 50 reach the target stage, the control module 40 can infuse the culture medium 60 from the perfusion flow channels 13 in reverse to flush the cell 50, and return the cells 50 to the culture medium infusion end 11. Therefore, the best growth cells 50 can be selected in the culture medium infusion end 11, to improve the probability of success and quality of subsequent cell culture.

For example, in the platform system for in vitro cell co-cultivation with automatic trapping function of the present disclosure, the endometrial cells are used as the base cells 51, and the fertilization embryos of mouse are used as cell 50 to be cultivated. However, these are taken as example for illustration, and the present disclosure is not limited thereto.

The kind of culture medium 60 can appropriately selected during the cultivate process. For example, during the cultivation of the base cells 51, the DMEM culture medium is cultivated uniformly in the cell co-cultivation platforms 20 to steady the endometrial cells, and construct a micro environment suitable for growth of the cells 50. In this case, the infused fluid flow of the culture medium 60 in dynamic perfusion culture is from 0.05 to 2 μl/min. According to the detection record by the microscope, the base cells 51 has stable growth in the second day, so it is time to infuse the cells 50 to be cultivated from the trapping flow channel module 30 to perform cell trapping. In implementation, the infused fluid flow of the cells 50 is from 0.01 to 1 μl/min. According to the detection result by the viewing equipment, the IC system of the present disclosure can respectively trap the cells 50 at the corresponding cell trapping areas 35 efficiently.

Next, the culture medium 60 is replaced by the M16 culture medium for co-cultivation of the endometrial cells and the embryonic cells. The infused fluid flow of the culture medium 60 of dynamic perfusion culture is from 0.01 to 1 μl/min, to replace the culture medium 60 timely, and to prevent the excrement caused by the cells and the death cell from heaping in the cell co-cultivation platforms 20 and impairing the cultivation quality.

According to the experiment result, the embryonic cell cultivated by the IC system of the present disclosure has higher growth speed than the cells cultivated in traditional petri dish. The embryo of mouse with eight cells can be cultivated to the blastula stage, so it can proved that the growth factor of the endometrial cell facilitates the growth of the embryonic cell, and it is also proved that the IC system of the present disclosure can construct a micro environment suitable for growth of the embryonic cell. The present disclosure can be applied to the field of bio-chip and cell culture, in particular to assisted reproductive technology (ART).

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A platform system for in vitro cell co-cultivation with automatic trapping function, comprising:
    a dynamic culture flow channel module, comprising a culture medium infusion end, a culture medium recovery end and a plurality of perfusion flow channels connecting the culture medium infusion end and the culture medium recovery end, and ends of the plurality of perfusion flow channels radially arranged around the culture medium infusion end, and other ends of the plurality of perfusion flow channels converged to the culture medium recovery end distantly located from the culture medium infusion end;
    a plurality of cell co-cultivation platforms, for co-cultivation of the plurality of base cells and a plurality of cell to be cultivated, and the plurality of cell co-cultivation platforms arranged around the culture medium infusion end, and the plurality of cell co-cultivation platforms being respectively passed through by the plurality of perfusion flow channels to correspondingly form a plurality of cell trapping areas; and
    a trapping flow channel module, comprising a cell infusion end, a cell inhalation end and a cell flow channel connecting the cell infusion end and the cell inhalation end, and the cell flow channel passing through the plurality of cell co-cultivation platforms, and surrounding outer side of the plurality of cell co-cultivation platforms annularly, and connected with the plurality of perfusion flow channels;
    wherein when a cell trapping process is performed, the culture medium infusion end and the culture medium recovery end are closed, and the cell infusion end and the cell inhalation end are opened, and then a plurality of cells are infused to be cultivated into the cell infusion end, and the plurality of cells to be cultivated flow through the plurality of cell co-cultivation platforms via the cell flow channel, and respectively stop at corresponding the plurality of cell trapping areas according to difference between dynamic flow resistances;
    after the plurality of cells to be cultivated are trapped at the plurality of cell trapping areas, the cell infusion end and the cell inhalation end are closed, and the culture medium infusion end and the culture medium recovery end are opened, and a culture medium is infused via the culture medium infusion end to perform a dynamic perfusion culture process for co-cultivation of the cells.

2. The platform system for in vitro cell co-cultivation with automatic trapping function according to claim 1, wherein the plurality of cells to be cultivated comprise embryonic cell, organ and tissue cell or stem cell.

3. The platform system for in vitro cell co-cultivation with automatic trapping function according to claim 1, wherein the plurality of base cells are a cell population for co-cultivation corresponding to the plurality of cells to be cultivated.

4. The platform system for in vitro cell co-cultivation with automatic trapping function according to claim 1, wherein structural size of each of the plurality of cell trapping area is smaller than size of each of the corresponding cells to be cultivated.

5. The platform system for in vitro cell co-cultivation with automatic trapping function according to claim 1, wherein when an initial culture process is performed on the plurality of cell co-cultivation platforms, the cell infusion end and the cell inhalation end are closed first, and then the culture medium containing the plurality of base cells is infused via the culture medium infusion end, and the culture medium flows into the plurality of cell co-cultivation platform, and the plurality of base cell respectively attach to the plurality of cell co-cultivation platforms to perform the initial culture process.

6. The platform system for in vitro cell co-cultivation with automatic trapping function according to claim 1, wherein after the plurality of cell to be cultivated are trapped at the cell trapping areas, the cells not trapping at the plurality of cell trapping areas are recovered at the cell inhalation end.

7. The platform system for in vitro cell co-cultivation with automatic trapping function according to claim 1, wherein the culture medium is infused via the plurality of perfusion flow channels, to flush the plurality of cells to be cultivated, to return the plurality of cells to be cultivated to the culture medium infusion end for further extraction.

8. The platform system for in vitro cell co-cultivation with automatic trapping function according to claim 1, wherein the infused fluid flow of the cells to be cultivated is from 0.05 to 10 μl/min.

9. The platform system for in vitro cell co-cultivation with automatic trapping function according to claim 1, wherein the infused fluid flow of the culture medium in dynamic perfusion culture process is from 0.01 to 5 μl/min.

* * * * *